United States Patent
Assmann

(10) Patent No.: US 8,363,916 B2
(45) Date of Patent: Jan. 29, 2013

(54) METHOD AND IMAGE PROCESSING SYSTEM FOR PRODUCING RESULT IMAGES OF AN EXAMINATION OBJECT

(75) Inventor: Stefan Assmann, Erlangen (DE)

(73) Assignee: Siemens Aktiengesllschaft, Munich (DE)

( * ) Notice: Subject to any disclaimer, the term of this patent is extended or adjusted under 35 U.S.C. 154(b) by 1160 days.

(21) Appl. No.: 12/000,649

(22) Filed: Dec. 14, 2007

(65) Prior Publication Data

US 2008/0170769 A1 Jul. 17, 2008

(30) Foreign Application Priority Data

Dec. 15, 2006 (DE) .......................... 10 2006 059 383

(51) Int. Cl.
*G06K 9/00* (2006.01)
(52) U.S. Cl. ........................................ 382/131; 382/128
(58) Field of Classification Search .................. 382/128, 382/131
See application file for complete search history.

(56) References Cited

U.S. PATENT DOCUMENTS

| | | | | |
|---|---|---|---|---|
| 6,978,039 | B2* | 12/2005 | Cline et al. ..................... | 382/128 |
| 7,158,692 | B2* | 1/2007 | Chalana et al. ................ | 382/294 |
| 7,336,809 | B2* | 2/2008 | Zeng et al. ..................... | 382/128 |
| 7,346,201 | B2* | 3/2008 | Ashton ........................... | 382/128 |
| 7,550,728 | B2* | 6/2009 | Spahn ....................... | 250/363.02 |
| 7,756,310 | B2* | 7/2010 | Manjeshwar et al. ........ | 382/128 |
| 7,822,246 | B2* | 10/2010 | Senegas et al. ................ | 382/128 |
| 7,835,782 | B2* | 11/2010 | Cherry et al. ................. | 600/411 |
| 7,873,195 | B2* | 1/2011 | Makram-Ebeid ............. | 382/128 |
| 7,899,231 | B2* | 3/2011 | Novak ........................... | 382/131 |
| 7,902,511 | B2* | 3/2011 | Thielemans et al. ..... | 250/363.04 |
| 8,208,987 | B2* | 6/2012 | Hengerer et al. .............. | 600/411 |
| 2003/0113003 | A1* | 6/2003 | Cline et al. ..................... | 382/128 |
| 2004/0242953 | A1* | 12/2004 | Good ................................ | 600/7 |
| 2005/0203420 | A1* | 9/2005 | Kleen et al. ..................... | 600/476 |
| 2005/0276455 | A1* | 12/2005 | Fidrich et al. .................. | 382/128 |
| 2006/0004275 | A1 | 1/2006 | Vija et al. | |
| 2006/0074290 | A1* | 4/2006 | Chen et al. ..................... | 600/407 |
| 2006/0100526 | A1* | 5/2006 | Yamamoto et al. ........... | 600/476 |
| 2006/0171578 | A1* | 8/2006 | Novak ........................... | 382/131 |
| 2006/0269130 | A1* | 11/2006 | Maroy et al. ................... | 382/173 |
| 2007/0019850 | A1* | 1/2007 | Knoplioch et al. ........... | 382/131 |

(Continued)

FOREIGN PATENT DOCUMENTS

DE 10357184 A1 7/2005

OTHER PUBLICATIONS

Wasserman, R.; Acharya, R.; Sibata, C.; Shin, K.H.; , "A data fusion approach to tumor delineation," Image Processing, 1995.*

*Primary Examiner* — David A Vanore
*Assistant Examiner* — Wyatt Stoffa
(74) *Attorney, Agent, or Firm* — Harness, Dickey & Pierce, P.L.C.

(57) ABSTRACT

At least one embodiment of the invention relates to a method for producing result images of an examination object, in the case of which a number of magnetic resonance images, determined by a magnetic resonance recording device, of the examination object are acquired, and radionuclide emission tomography image data, determined by a radionuclide emission tomography recording device, of the examination object are acquired. In at least one embodiment, the magnetic resonance images for determining contours of a target structure are then segmented, and the contours of the target structure are visualized in common with at least the radionuclide emission tomography image data that are assigned to picture elements located inside the target structure, and/or are stored for a later visualization. Moreover, a corresponding image processing system and an imaging system having such an image processing system are described in at least one embodiment.

8 Claims, 3 Drawing Sheets

U.S. PATENT DOCUMENTS

| | | | |
|---|---|---|---|
| 2007/0066899 A1* | 3/2007 | Boese et al. | 600/439 |
| 2007/0116338 A1* | 5/2007 | Fidrich et al. | 382/128 |
| 2007/0218002 A1* | 9/2007 | Barrio et al. | 424/9.1 |
| 2007/0230765 A1* | 10/2007 | Wang et al. | 382/132 |
| 2008/0025584 A1* | 1/2008 | Kunz et al. | 382/128 |
| 2008/0050000 A1* | 2/2008 | Blaffert et al. | 382/131 |
| 2008/0056550 A1* | 3/2008 | Kadir et al. | 382/131 |
| 2008/0069414 A1* | 3/2008 | Manjeshwar et al. | 382/128 |
| 2008/0170769 A1* | 7/2008 | Assmann | 382/128 |
| 2008/0214927 A1* | 9/2008 | Cherry et al. | 600/411 |
| 2009/0030304 A1* | 1/2009 | Feiweier et al. | 600/411 |
| 2009/0122060 A1* | 5/2009 | Porat et al. | 345/424 |
| 2010/0204563 A1* | 8/2010 | Stodilka et al. | 600/411 |

* cited by examiner

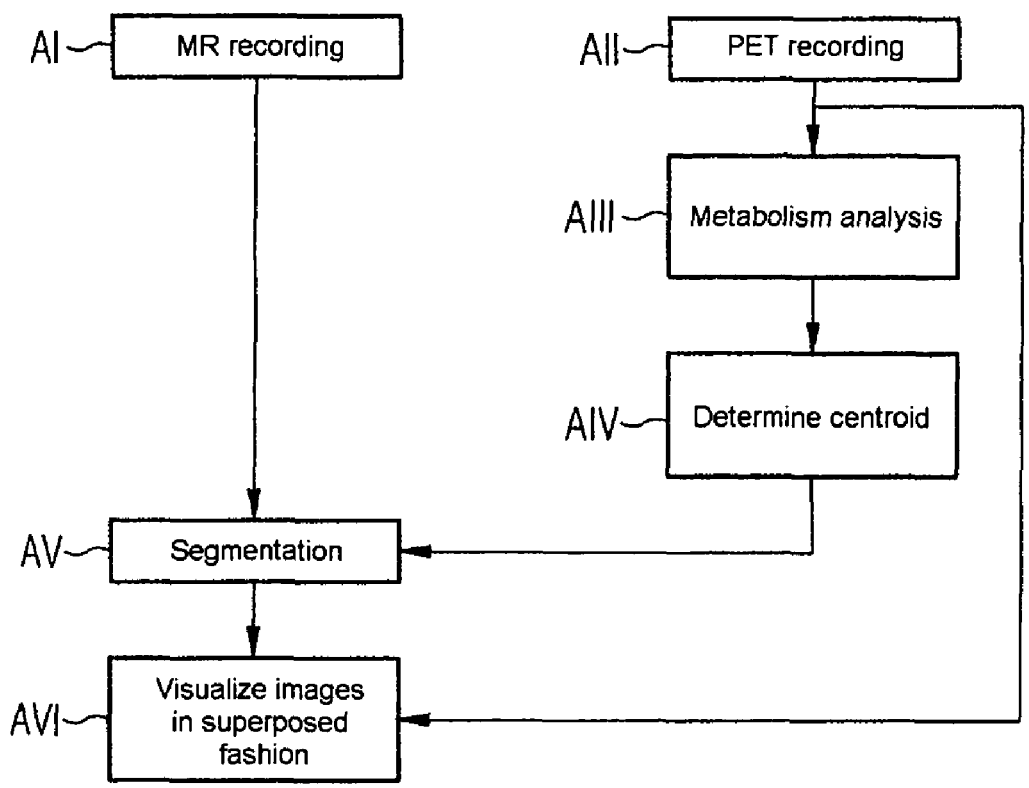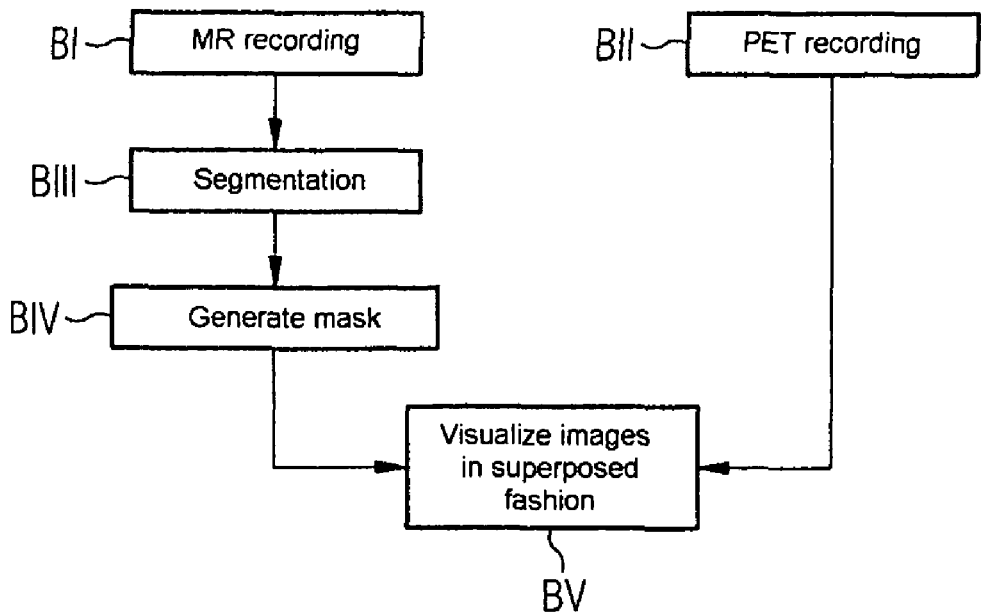

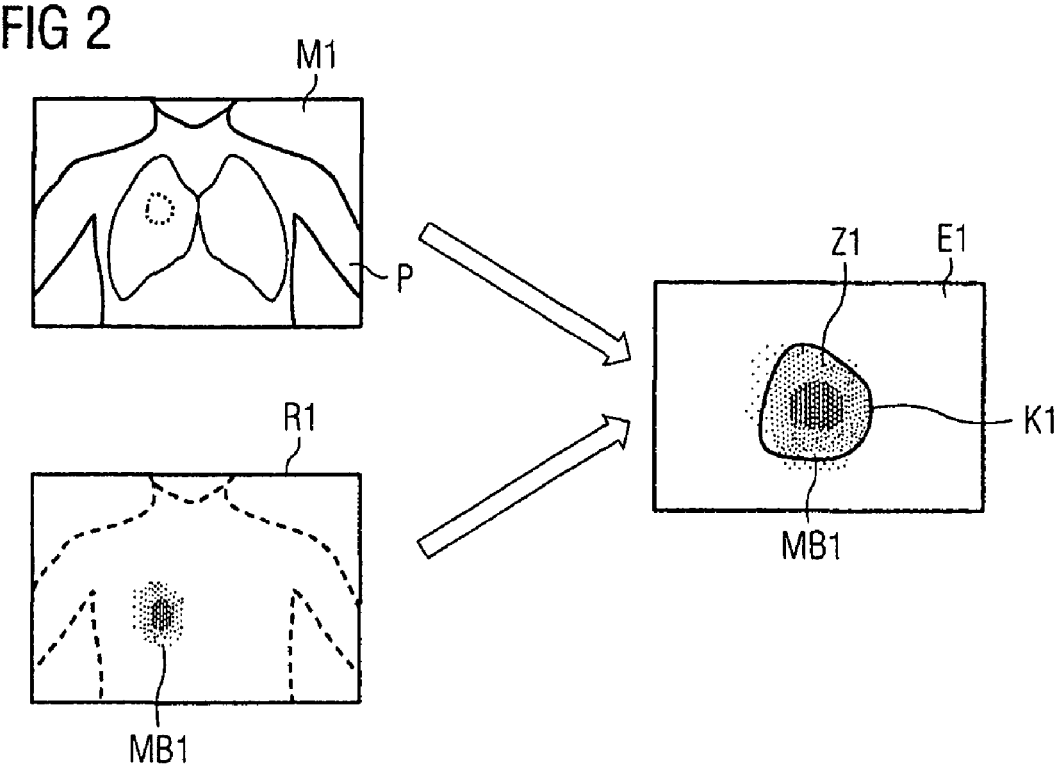
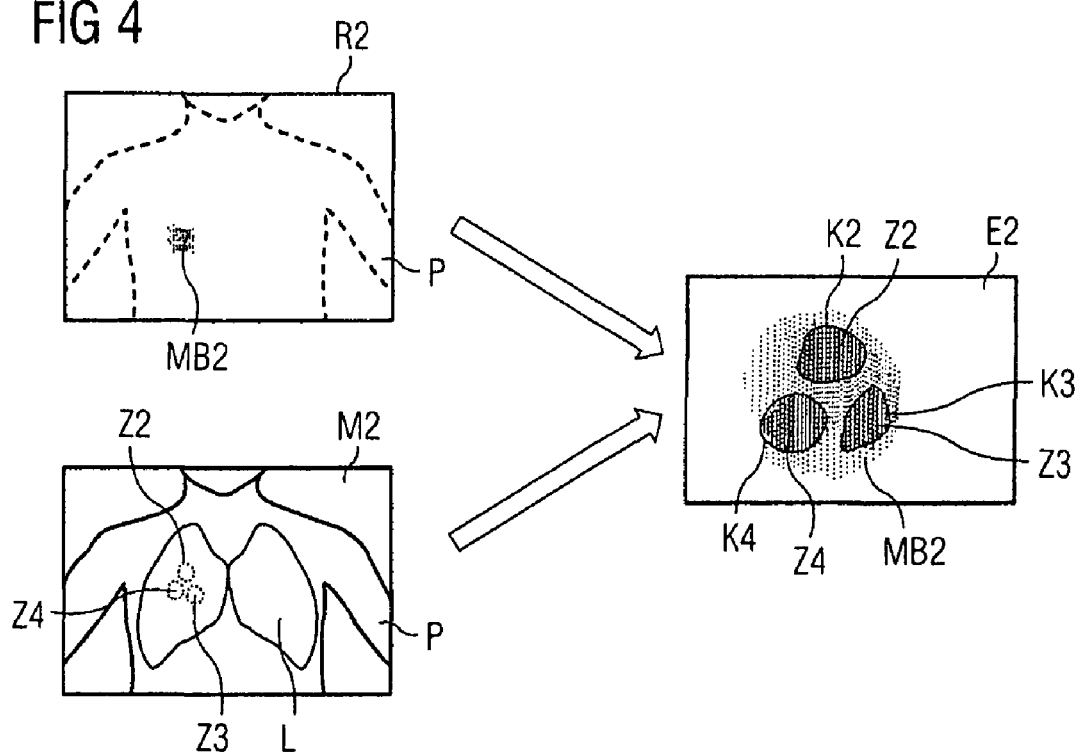

METHOD AND IMAGE PROCESSING SYSTEM FOR PRODUCING RESULT IMAGES OF AN EXAMINATION OBJECT

PRIORITY STATEMENT

The present application hereby claims priority under 35 U.S.C. §119 on German patent application number DE 10 2006 059 383.9 filed Dec. 15, 2006, the entire contents of which is hereby incorporated herein by reference.

FIELD

Embodiments of the invention generally relate to a method for producing result images of an examination object. For example, they may relate to one wherein, firstly, a number of magnetic resonance images of the examination object and, secondly, radionuclide emission tomography image data of the examination object are acquired, and combined images are then produced with the aid of these image data. Moreover, embodiments of the invention generally relate to a corresponding image processing system for carrying out this method, and/or to an imaging system having such an image processing system.

BACKGROUND

There have currently been developed in medicine a whole series of imaging systems that can be used to take pictures of the interior of the body of a patient. These include, for example, the magnetic resonance units and radionuclide emission tomography recording devices named at the beginning. Among these are PET systems (PET=Positron Emission Tomography) and SPECT systems (SPECT=Single Photon Emission Computer Tomography), in the case of which small amounts of specific substances provided with radioactive materials, so-called "tracers", are injected into the human body in order to detect various metabolisms in the body by measuring the radioactive radiation.

The amount of injected material is extremely small and lies in the subphysiological range. Consequently, no influencing of the metabolic process to be examined comes about, nor do toxic reactions occur. The weakly radioactive radiation is registered with the aid of scintillation detectors, and an image is produced therefrom. The tracer accumulates in specific organs and/or tumors, and thus permits a very good diagnosis of the metabolisms and, in particular, a very easy and exact detection of tumors and metastases in the surrounding tissue.

Such methods can also be used, for example, to assess the flow of blood to the cardiac muscle. Whereas in the case of magnetic resonance tomography, it is possible to produce a relatively well spatially resolved image data record in which specific structures, for example specific organs, can be detected particularly well, PET and SPECT systems are, by contrast, used to produce images in which specific pathological changes can be identified. Specifically, an exact identification of metabolisms that indicate a pathological change is not directly possible with the aid of normal magnetic resonance methods. Consequently, both magnetic resonance images and radionuclide emission tomography image data of an examination object are meanwhile being acquired ever more frequently and are being adapted to one another such that they can be superposed in an image in a fashion true to location.

These images, which contain the mutually adapted information from various recording methods are denoted below as examination result images or, for short, as "result images".

Such image fusion methods also exist for images from other image recording devices. Thus, for example, DE 103 57 184 A1 describes a method in which magnetic resonance images of the interior of a hollow organ are superposed on 3D-fluorescence images that have been made with the aid of an instrument to be introduced invasively into the same body region.

The mutual geometric adaptation, required for superposition, of the image data of the individual images, which is usually also denoted as "registration" of the images, requires a substantial outlay on computation. Consequently, it is proposed in US 2006/0004275 A1 that instead of the complete PET and/or SPECT images, on the one hand, and magnetic resonance images, on the other hand, only previously selected image regions of interest, so-called "Regions of Interest" (ROI) or "Volumes of Interest" (VOI), of the respective images or image data records are being registered on one another and are being superimposed. These ROI or VOI are fixed manually by the user with the aid of a graphical operator interface.

There have already currently been developed combined imaging systems that have both a magnetic resonance recording device and a radionuclide emission tomography recording device. However, here, as well, the magnetic resonance images and the radionuclide emission tomography image data are firstly processed completely separately and subsequently superposed. The advantage of these systems resides, however, in that because they have been prepared on the same system, the images are already registered in terms of hardware and thus can more easily be superposed in a fashion true to location.

SUMMARY

In at least one embodiment, the present invention creates an improved method for producing such combined result images, and/or a corresponding image processing system for carrying out such a method. For example, such a system can better use the available resources without a large extra outlay in order to produce images that are more informative in a simpler and easier way.

As already described above, it has so far been customary only to superpose radionuclide emission tomography image data on complete magnetic resonance images in order thus to be able the better to identify specific metabolic accumulations inside the magnetic resonance images.

In contrast thereto, according to an embodiment of the invention, the magnetic resonance images are being segmented in order to determine contours of a target structure, and the contours of the target structure from the magnetic resonance images and, if appropriate, also the complete magnetic resonance image with the contours therein, in common with at least the radionuclide emission tomography image data that are assigned picture elements located inside the target structure are now visualized and/or stored for a later visualization. The term "picture elements" is to be understood here either as two-dimensional picture elements (so-called pixels) or three-dimensional picture elements (so-called voxels). It is likewise possible in the case of the magnetic resonance images, the radionuclide emission tomography images or the result images for two-dimensional tomograms or three-dimensional image data records, for example, to be involved.

In many cases, magnetic resonance images are in any case already to be further processed during or immediately after the examination in the interest of further planning of the examination, for making a diagnosis, for preparing operations and/or for monitoring the progress of illnesses, in which case a particular role is played by the so-called "segmentation" of anatomical structures and/or of pathological structures and/or foreign body structures. In the case of such a segmentation, the image data of the examination object are broken down such that the selected target structures are separated from the remaining image data. A clear example of this is the separation of a specific bone structure, for example the ethmoid bone from a magnetic resonance data record of the head of a patient. Further examples are the separation of the lung from an upper body magnetic resonance data record of the patient, or the separation or graphic accentuation of a tumor inside an organ.

In accordance with at least one embodiment of the invention, the aim now is to combine this segmentation of the magnetic resonance images with the radionuclide emission tomography image data such that, finally, result images are produced that reproduce the contours of the target structure as accurately as possible and, at the same time, permit an analysis of the constituents of the target structure. Such images are exceptionally helpful for a diagnosis and for planning operations and treatment.

To this end, the inventive image processing system requires an interface for acquiring magnetic resonance images, determined by means of a magnetic resonance recording device, of the examination object, and an interface for acquiring radionuclide emission tomography image data, determined by means of a radionuclide emission tomography recording device, of the examination object. This can involve separate interfaces, but also a common interface that is capable of retrieving corresponding data from the recording devices or from image data memories in which the image data have already been filed.

Furthermore, this image processing system requires a segmentation unit for segmenting the magnetic resonance images for determining contours of a target structure, and an image fusion device for visualizing the contours of the target structure from the magnetic resonance images in common with at least the radionuclide emission tomography image data that are assigned to picture elements located inside the target structure, and/or for storing for a later visualization. Finally, this image fusion device superposes the data on one another and thereby produces the finished result images that are then sent for the purpose of direct visualization to a corresponding unit with a display, for example a classification station, or to an image memory, from which they can then be called up later.

There are two example embodiments of variants for implementing the invention.

In the first variant, the segmentation of the magnetic resonance images is performed by using the radionuclide emission tomography image data. Segmentation of tomographic data is known to be a non-trivial problem. An entire range of different methods are available in this case.

Thus, for example, there are the simple point oriented methods that use the intensity value of a picture element as a segmentation feature. In this case, each picture element is viewed in isolation, and a threshold value is used to classify the individual picture elements with regard to their belonging to a target structure. The optimum selection of the threshold value is critical in this case for a segmentation that is as free from error as possible.

Moreover, there are edge oriented methods in the case of which edges are detected or are tracked, for example via active contours.

Furthermore, so-called region oriented methods are known in which regions are detected whose picture elements have an identical feature. Here, as well, intensity values frequently serve as features. The best known region oriented method is the so-called region growth method, which will be explained in more detail later.

Furthermore, there are knowledge based methods that feature prior knowledge, for example in the form of a model of the structure to be segmented that is adapted to the tomographic data. However, such knowledge based methods are often unsuitable for segmentation of the shape or position of greatly varying objects, for example of pathological changes such as tumors.

As follows from the above explanations, specific parameters such as, for example, at least a starting point and/or a specific threshold value must be prescribed for most segmentation methods. Consequently, in the case of an example method, a corresponding suitable parameter is determined for segmentation on the basis of the radionuclide emission tomography image data, and this parameter is then used in the segmentation of the magnetic resonance images.

For example, an accumulation of specific metabolisms can firstly be sought inside the radionuclide emission tomography image data. The coordinates of the picture elements at which this metabolic accumulation takes place are then known. It is therefore possible to determine on the basis of these coordinates a number of picture elements in the magnetic resonance images from which, in turn, a specific characteristic feature is then extracted that, finally, is used as parameter for the segmentation.

In a particularly preferred example variant, the segmentation of the magnetic resonance images is performed with the aid of a region growth method. To this end, a starting point for the region growth method is determined on the basis of the radionuclide emission tomography image data. If, for example, there is present in the radionuclide emission tomography image data a tumor that constitutes a focus on the basis of its metabolic accumulation, a midpoint or centroid of the relevant focus can be determined inside the radionuclide emission tomography image data. This picture element can then be transmitted to the magnetic resonance image data and be used as starting point for the segmentation of the relevant tumor.

Thus, the size and exact shape of the tumor are determined automatically as a result from the magnetic resonance image data, and the details relating to the metabolism of the tumor, that is to say its composition and thus the type of the tumor, are known from the radionuclide emission tomography image data. A diagnosis or planning of operations or treatments is possible on the basis of such data in a relatively effective and reliable fashion. The method also has the advantage that it can be carried out with a relatively low outlay on computation.

In the second example variant, the magnetic resonance images are firstly segmented independently of the radionuclide emission tomography image data. A mask that is superposed in a common image on the radionuclide emission tomography image data is compiled on the basis of the contours of the target structure that are determined in the process. In conventional radionuclide emission tomography images, to be specific, the poor spatial resolution generally means that it is not individual tumors which are visible, but only a spatially unspecifiable accumulation of increased metabolism. By displaying the contours from the magnetic resonance images, it is thus possible to determine whether what is involved is an individual tumor or a number of tumors and—if the latter is the case—which part of the metabolic accumulation stems from which tumor.

It is fundamentally possible with both methods that both the complete magnetic resonance images and the complete radionuclide emission tomography image data are reproduced in the result images, the contours of the target structure that have been determined in the segmentation method, or the entire target structure being given prominence, that is to say, for example, being intensified or emphasized compared to the surroundings. Likewise, a display having only the image data of the target structure is also possible, it being possible, in turn, to emphasize the contours.

In the case of a preferred example variant, however, it is only the radionuclide emission tomography image data which are located inside the target structure that are visualized with the contours of the target structure and/or are stored for a later visualization. If required, however, it is also possible, as previously described, for further parts of the magnetic resonance image to be displayed, as well, in order to be able to display the structure inside its surroundings more effectively. For example, the exact structure of a tumor can thus be visualized inside the structure of the surrounding organ, and thus its position in the organ can be visualized.

The inventive image processing system of at least one embodiment can be implemented in principle on any existing image computer that can previously already be used for magnetic resonance image processing with different methods. In this case, it is also possible to update an existing image processing system to provide an inventive image processing system with the aid of a corresponding computer program product in which the interfaces, the segmentation unit and the image fusion device are implemented in the form of software components.

Such an inventive image processing system can, in particular, also be part of an imaging system that has a magnetic resonance recording device and a radionuclide emission tomography recording device such that the image data produced by these recording devices can be transferred immediately to the image processing system. In principle, the image processing system can, however, also be designed as a separate device that subsequently inventively processes already present magnetic resonance images and radionuclide emission tomography image data of a specific examination object.

BRIEF DESCRIPTION OF THE DRAWINGS

The invention is explained in more detail below with the aid of example embodiments and with reference to the attached drawings, in which:

FIG. 1 shows a flowchart for illustrating a possible sequence of an embodiment of the inventive method according to a first variant, FIG. 2 shows a schematic of the combination of a PET image and an MR image in accordance with the method according to FIG. 1, FIG. 3 shows a flowchart for illustrating a possible sequence of an embodiment of the inventive method according to a second variant, FIG. 4 shows a schematic of the combination of a PET image and an MR image in accordance with an embodiment of the method according to FIG. 3.

DETAILED DESCRIPTION OF THE EXAMPLE EMBODIMENTS

Figure 5:
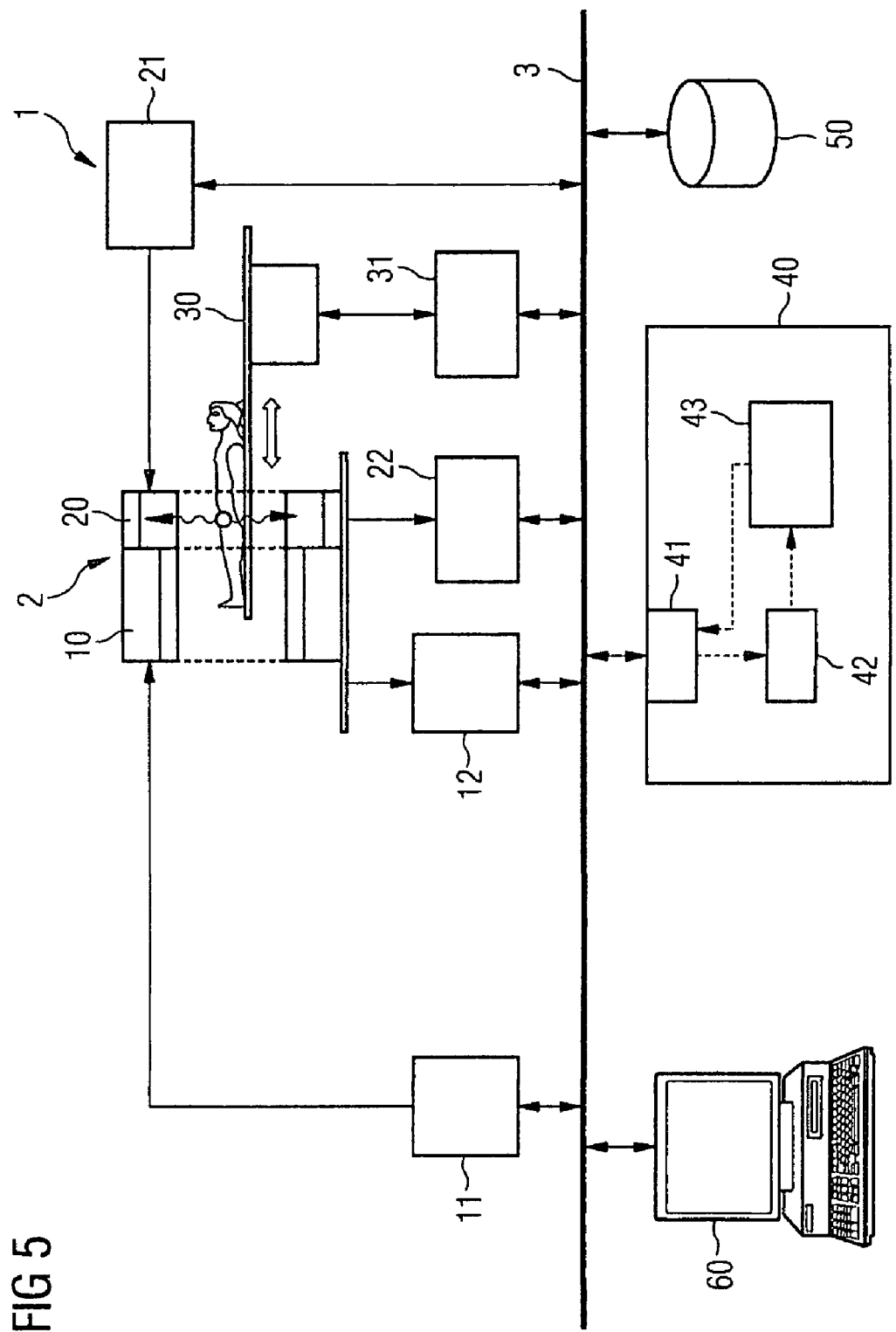
FIG. 5 shows a schematic of an example embodiment of an inventive image processing system.

The terminology used herein is for the purpose of describing particular embodiments only and is not intended to be limiting of the present invention. As used herein, the singular forms "a", "an", and "the" are intended to include the plural forms as well, unless the context clearly indicates otherwise.

It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

As already described at the beginning, the radionuclide emission tomography methods include the so-called PET methods and SPECT methods. Since PET methods are much more frequently applied in practice, it is assumed below without restricting the invention thereto that the radionuclide emission tomography recording device is a PET recording device, and that corresponding PET image data are available.

A first variant of an embodiment of the inventive method becomes clear with the aid of FIGS. 1 and 2. In this method, a magnetic resonance picture is taken in a first method step AI. In a further method step AII that can precede or follow the first-named method step AI or take place simultaneously, PET data of the same examination region of the same patient are acquired as with the magnetic resonance recording. As an example, to this end FIG. 2 shows very schematically a magnetic resonance image ("MR image" below) M1 of the upper body of a patient P, and a corresponding PET image R1 of the upper body of the same patient P. The lung L of the patient P can be seen in the MR image, there being visible inside the lung L a specific, not exactly identifiable target structure Z1 that is suspected of being pathological. By contrast, only an accumulation of specific metabolisms MB1 can be seen in the PET image.

These metabolisms MB1 are analyzed in a method step AIII (see FIG. 1), and a centroid of a metabolic accumulation or, if appropriate, also a number of centroids of specific "clumps" of metabolisms are then determined in step AIV.

These coordinates of the centroid or the centroids found are then used in step AV to segment the MR image M1. Here, the centroids serve respectively as starting points for a region growth method. To this end, proceeding from the respective starting point for each neighboring pixel or voxel, a check is made as to whether a homogeneity criterion is fulfilled, that is to say as to whether there is a sufficiently great similarity with the features of the pixel or voxel at the starting point. If this is the case, the new pixel or voxel is added to the segment, and all the neighboring picture elements are checked for their similarity. If a picture element does not fulfill the homogeneity criterion, no further check in the neighborhood is carried out starting from this point.

If a number of starting points are selected in order to segment a target structure, it is possible in this case also to combine and average the features of these starting points in order thus to find the homogeneity criterion. However, each starting point can also alternatively be assigned to exactly one target structure in order thus to find a number of target structures.

Various suitable algorithms for carrying out the region growth method are known to the person skilled in the art and therefore need not be explained here in detail.

The segmented magnetic resonance image thus obtained, or else only the target structure Z1 with its contours K1 is then displayed in common with the PET image data in a result image E1.

With the aid of this image E1, the user can not only detect the precise shape and size of the target structure, but also determine information as exact as possible in relation to the type of tissue on the basis of the metabolite data. Represented here in a simplified way, it need not necessarily be a two-dimensional segmentation that is involved in this case, but a three-dimensional segmentation can also be involved, it being possible for the three-dimensional target structure in the result image for example, to be rotated virtually in space on a display screen and be viewed from various sides, and for various sections through the target structure to be displayed.

FIGS. 3 and 4 show the principle of an alternative method. Here, as well, an MR picture and a PET picture are produced in steps BI and BII. These images M2, R2 are illustrated schematically in FIG. 4.

Three unknown target structures Z2, Z3, Z4 that indicate the existence of tumors are located in the lung in the magnetic resonance image M2 shown in FIG. 4 (here, as well, merely in a two-dimensional illustration again, 3D-illustration likewise being possible).

Thereupon, in method step BIII, the target structures z2, Z3, Z4 in the magnetic resonance image data are firstly segmented independently of the PET image data, the exact contours K2, K3, K4 of the three target structures Z2, Z3, Z4 being determined. The person skilled in the art is aware of a multiplicity of suitable segmentation methods to this end.

Also to be detected in the PET image R2 at the same point is an accumulation of metabolisms MB2 that cannot be exactly assigned in space. In order to identify these more accurately, an image mask is compiled on the basis of the contours K2, K3, K4 of the target structures Z2, Z3, Z4 of the MR image M2, and is superposed with the PET image R2 in a result image E2. That is to say, the contours K2, K3, K4 of the target structures Z2, Z3, Z4 from the magnetic resonance image M2 are superposed with the accumulation of metabolisms MB2 such that the various tumors are displayed individually in a resolved fashion inside the metabolic accumulation. It may thus be detected whether the metabolic accumulation involves one or more tumors, and if yes where these precisely lie and to what type they correspond.

As illustrated here in a simplified way, the result image E2 produced in this second variant of an embodiment of the inventive method need not be a two-dimensional image, but it can also be a question of a three-dimensional image data record, it being possible for the three-dimensional target structure in the result image to be rotated virtually in space on a display screen and to be viewed from various sides, and for various sections through the target structures to be displayed.

It quickly becomes clear from the above named examples that a very good tool is made available with the aid of an embodiment of the inventive method for the purpose of combining MR images and PET images (or SPECT images) such that the mutually complementary image data are optimally employed.

An imaging system with the aid of which such a method can be carried out is shown in a very approximate schematic in FIG. 5. This system here comprises a combined image recording device 2 that consists of a magnetic resonance recording device 10 and a PET recording device 20. The modes of operation of these devices are known in principle to the person skilled in the art, and have no need here of further explanation. A patient/subject P can be moved to and fro via a patient couch 30 between the two units 10, 20 such that the various pictures can be taken one after another. Since all the spatial coordinates relating to the desk position 30 are known, it is possible in this case for the respectively produced images to be registered, that is to say adapted to one another, automatically in order to superpose them in a fashion true to location or to convert the positions in one image into the position of the respective other image.

The couch 30 is controlled via a couch control device 31, the PET recording device 20 via a PET control device 21 and the MR recording device 10 via an MR control device 11. The image data acquisition of the PET data is performed with the aid of a PET image data acquisition unit 22, and the image data of the MR unit 10 are acquired with the aid of an MR image data acquisition unit 12. All the components are connected via a data bus 3 to a central computer 60 from which the operation of the system 1 can be performed. Moreover, an image memory 50 is connected to this bus 3.

A further essential component here is an image processing system 40 that acquires both the magnetic resonance images and the PET image data via an interface 41. These image data are then passed on to a segmentation unit 42 in which the segmentation is carried out according to one of the methods previously described. In an image fusion device 43, the images are superposed and, for example, transmitted via the interface 41 to the computer 60 so that they can be output there on a display screen to the user. Alternatively or in addition, these finished result images can also be filed in the computer 50.

The input image data, that is to say the PET image data and the magnetic resonance images that are used inside the image processing device in order to produce the result images, can in this case be retrieved directly by the image data acquisition units 22, 12 of the PET recording device 20 and the MR recording device 10, or be called up from the image memory 50 in which they have previously been filed.

Finally, it may be pointed out once again that the method previously described in detail and the system architecture are only preferred exemplary embodiments that can be modified by the person skilled in the art in the most varied ways without departing from the scope of the invention to the extent it is prescribed by the claims. For the sake of completeness, it may also be pointed out that the use of the indefinite article "a/an" does not preclude that the relevant features can be on hand more than once.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing result images of an examination object, the method comprising:
   acquiring a number of magnetic resonance images, determined by a magnetic resonance recording device, of the examination object;
   acquiring radionuclide emission tomography image data, determined by a radionuclide emission tomography recording device, of the examination object;
   segmenting the magnetic resonance images to determine contours of a target structure, wherein the segmentation of the magnetic resonance images includes region growth, and a starting point for the region growth being a central part of a focus in the radionuclide emission tomography image data; and
   at least one of
   visualizing the contours of the target structure in common with at least the radionuclide emission tomography image data assigned to picture elements located inside the target structure, and
   storing the contours for a later visualization.

2. The method as claimed in claim 1, wherein only the radionuclide emission tomography image data that are assigned for picture elements located inside the target structure are at least one of visualized with the contours of the target structure and, if appropriate, the relevant magnetic resonance image, and stored for a later visualization.

3. An image processing system for producing result images of an examination object, comprising:
   an interface to acquire magnetic resonance images, determined by a magnetic resonance recording device, of the examination object;
   an interface to acquire radionuclide emission tomography image data, determined by a radionuclide emission tomography recording device, of the examination object;
   a segmentation unit to segment the magnetic resonance images to determine contours of a target structure using region growth, a starting point for the region growth being a central part of a focus in the radionuclide emission tomography image data; and
   an image fusion unit at least one of to visualize the contours of the target structure from the magnetic resonance images in common with at least the radionuclide emission tomography image data that are assigned to picture elements located inside the target structure, and to store the contours for a later visualization.

4. An imaging system for producing result images of an examination object, comprising:
   a magnetic resonance recording device;
   a radionuclide emission tomography recording device; and
   an image processing system as claimed in claim 3.

5. A non-transitory computer program product configured to be loaded directly into a memory of an image processing system, including program code segments for executing all the steps of method as claimed in claim 1 when the program product is executed on the image processing system.

6. An image processing system for producing result images of an examination object, comprising:
   means for acquiring magnetic resonance images, determined by a magnetic resonance recording device, of the examination object;
   means for acquiring radionuclide emission tomography image data, determined by a radionuclide emission tomography recording device, of the examination object;
   means for segmenting the magnetic resonance images to determine contours of a target structure, wherein the segmentation of the magnetic resonance images includes region growth, and a starting point for the region growth being a central part of a focus in the radionuclide emission tomography image data; and
   means for at least one of visualizing the contours of the target structure from the magnetic resonance images in common with at least the radionuclide emission tomography image data that are assigned to picture elements located inside the target structure, and storing the contours for a later visualization.

7. An imaging system for producing result images of an examination object, comprising:
 a magnetic resonance recording device;
 a radionuclide emission tomography recording device; and
 an image processing system as claimed in claim 6.

8. A non-transitory computer readable medium including program segments for, when executed on a computer device of an image processing system, causing the computer device to implement the method of claim 1.

* * * * *

UNITED STATES PATENT AND TRADEMARK OFFICE
CERTIFICATE OF CORRECTION

| | | |
|---|---|---|
| PATENT NO. | : 8,363,916 B2 | Page 1 of 1 |
| APPLICATION NO. | : 12/000649 | |
| DATED | : January 29, 2013 | |
| INVENTOR(S) | : Stefan Assmann | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1290 days.

Signed and Sealed this
Eighteenth Day of November, 2014

Michelle K. Lee
*Deputy Director of the United States Patent and Trademark Office*